United States Patent
Venkatesan

Patent Number: 6,020,361
Date of Patent: Feb. 1, 2000

[54] SUBSTITUTED BENZO[1,4]DIOXINES AS ANTIOBESITY AGENTS

[75] Inventor: Aranapakam M. Venkatesan, Rego Park, N.Y.

[73] Assignee: America Home Products Corp., Madison, N.J.

[21] Appl. No.: 09/323,463

[22] Filed: Jun. 1, 1999

Related U.S. Application Data

[62] Division of application No. 08/993,481, Dec. 18, 1997, Pat. No. 5,965,607.
[60] Provisional application No. 60/034,085, Dec. 30, 1996.

[51] Int. Cl.[7] .................................................. A61K 31/335
[52] U.S. Cl. ............................................................ 514/452
[58] Field of Search ............................................ 514/452

[56] References Cited

U.S. PATENT DOCUMENTS

| | | | |
|---|---|---|---|
| 5,061,727 | 10/1991 | Bloom | 514/465 |
| 5,482,971 | 1/1996 | Epstein | 514/465 |

FOREIGN PATENT DOCUMENTS

| | | |
|---|---|---|
| 0825189 | 2/1998 | European Pat. Off. . |
| 9635685 | 11/1996 | WIPO . |

OTHER PUBLICATIONS

Bloom et al., J. Med. Chem. 192, vol. 35, No. 16, pp. 3081–3084.
Bloom et al., Drugs of the Future, 1994, vol. 19(1), 23–26.
Emorine et al., Science, 1989, vol. 245, No. 8, pp. 1118–1121.
Largis et al., Drug Development Research, 1994, vol. 32, 69–76.

*Primary Examiner*—Jerome D. Goldberg
*Attorney, Agent, or Firm*—Daniel B. Moran

[57] ABSTRACT

This invention relates to novel substituted 1,4-benzodioxine compounds having antidiabetic, andihyperglycemic, and antiobesity properties represented by the formula

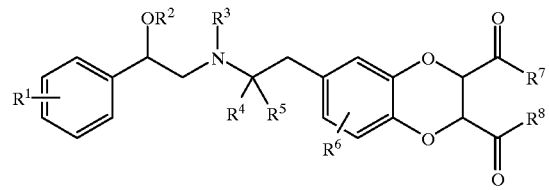

wherein $R^1$ and $R^6$ are independently hydrogen, $C_1$ to $C_6$ alkyl, trifluoromethyl, cyano, $C_1$ to $C_6$ alkoxy, or halogen;

$R^2$ is hydrogen or $C_1$ to $C_6$ trialkylsilyl; $R^3$ is hydrogen or $C_1$ to $C_6$ alkoxycarbonyl;

or $R^2$ and $R^3$ are joined to form the oxazolidinone ring

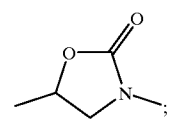

$R^4$ and $R^5$ are independently hydrogen or $C_1$ to $C_6$ alkyl; $R^7$ and $R^8$ are independently hydrogen $OR^9$ or $NR^{10}R^{11}$;

$R^9$ is hydrogen, $C_1$ to $C_{12}$ alkyl, $C_1$ to $C_{12}$ cycloalkyl, $C_1$ to $C_{12}$ silylalkyl, phenyl, naphthyl, phenyl $C_1$ to $C_6$ alkyl, $C_1$ to $C_6$ alkoxy $C_1$ to $C_6$ alkyl, pyridyl, thiophenyl, furanyl, imidazolyl, oxazolyl, $-CHR^{12}COOR^{13}$, $-CHR^{12}C(O)R^{13}$, $-CHR^{12}CONR^{10}R^{11}$, $-CHR^{12}OCOOR^{13}$, or $-CHR^{12}OC(O)R^{13}$; $R^{10}$ and $R^{11}$ are independently hydrogen, $C_1$ to $C_{12}$ alkyl, phenyl, naphthyl, phenyl-$C_1$ to $C_6$ alkyl, furanylalkyl, or alkoxycarbonylalkyl;

$R^{12}$ and $R^{13}$ are independently hydrogen, $C_1$ to $C_{12}$ alkyl, phenyl, naphthyl, or phenyl-$C_1$ to $C_6$ alkyl; and the pharmaceutically acceptable salts thereof, a salt thereof;

an enantiomer thereof, the racemic mixtures thereof, and the diastereomeric mixtures thereof.

The present invention also relates to a pharmaceutical composition, and methods for treating diabetes and/or hyperglycemia and/or obesity in mammals and producing lean meat in edible domestic animals.

11 Claims, No Drawings

SUBSTITUTED BENZO[1,4]DIOXINES AS ANTIOBESITY AGENTS

This application claims the benefit of priority of provisional application number 60/034,085 filed on Dec. 30, 1996.

This is a divisional of copending application(s) Ser. No. 08/993,481 filed on Dec. 18, 1997, now U.S. Pat. No. 5,965,607, the entire disclosure of which is hereby incorporated by reference.

This invention relates to novel substituted 1,4-benzodioxine compounds which have antidiabetic, antihyperglycemic, and antiobesity properties. The present invention also relates to pharmaceutical compositions comprising these compounds, methods for the preparation of these compounds, and methods for the use of these compounds in treating diabetes and/or hyperglycemia and/or obesity in mammals. The antiobesity compounds may find further use in reducing the fat content in domestic edible animals.

BACKGROUND OF THE INVENTION

It is well known that medicinal agents are employed in the treatment of persons suffering from diabetes, hyperglycemia, and obesity. The compounds of the present invention achieve their antidiabetic, antihyperglycemic, and antiobesity effects by acting as selective agonists at $\beta_3$ adrenergic receptors. The stimulation of these receptors on white and brown adipocytes promotes both lipolysis (breakdown of fat) and energy expenditure. Selective stimulation of $\beta_3$ adrenergic receptors is important for chronic treatment. Stimulation of other $\beta$-receptors could cause side effects such as increased heart rate ($\beta_1$ effect) and/or muscle tremor ($\beta_2$ effect). The compounds of the present invention show high selectivity for $\beta_3$ adrenergic receptors.

Bloom, et al., U.S. Pat. No. 5,061,727, disclose substituted 5-(2-((2-aryl-2-hydroxyethyl)amino)propyl)-1,3-benzodioxoles of general formula (I)

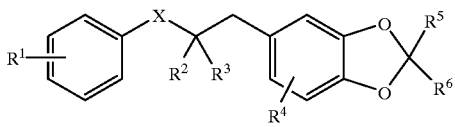

wherein $R^1$ and $R^4$ may be one or more groups which may be the same or different and are selected from the group consisting of hydrogen, $C_1$ to $C_4$ alkyl, $C_1$ to $C_4$ alkoxy, hydroxy, halogen, trifluoromethyl, carboxy, hydroxyalkyl, alkoxycarbonyl, $C_1$ to $C_4$ thioalkyl, sulfonyl and sulfinyl; X is a divalent radical consisting of

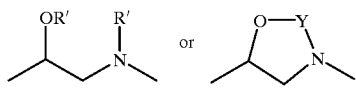

wherein R' is selected from the group consisting of hydrogen, $C_1$ to C4 alkyl and $C_1$ to $C_4$ acyl and Y is selected from the group consisting of carbonyl and thiocarbonyl; $R^2$ and $R^3$ may be the same or different and are selected from the group consisting of hydrogen and $C_1$ to $C_4$ alkyl; $R^5$ and $R^6$ are selected from the group consisting of hydrogen, carboxy, alkoxycarbonyl, hydroxymethyl, —CH$_2$OCH$_2$COOR$_7$ and —CH$_2$OCH$_2$CH$_2$OR$_7$, where $R^7$ is hydrogen or $C_1$ to $C_4$ alkyl; with the provision that $R^5$ and $R^6$ may not both be hydrogen; which have antihyperglycemic and antiobesity activity.

The synthesis, antidiabetic effects, and antiobesity effects of (R,R)-5-[2-[[2-(3-chlorophenyl)-2-hydroxyethyl]amino] propyl]-1,3-benzodioxole-2,2-dicarboxylate, disclosed by Bloom, et al. in U.S. Pat. No. 5,061,727, are detailed in Bloom, et al. *J. Med. Chem.*, 1992, 35, 3081, Largis, et al. *Drug Dev. Res.*, 1994, 32, 69, and Bloom, et al. *Drugs of the Future*, 1994, 19, 23.

The compounds of the present invention contain a 1,4-benzodioxine ring, whereas the compounds in Bloom, et al., U.S. Pat. No. 5,061,727 contain a 1,3-benzodioxole. They retain high selectivity for the $\beta_3$ receptor and show much higher antiobesity and antihyperglycemic activity in animal models. Therefore, the compounds of this invention are useful in treating diabetes, hyperglycemia, and obesity, exhibiting minimal side effects such as heart rate increase and/or muscle tremor in humans and animals, when formulated into pharmaceutical compositions. Health-conscious individuals today are making an effort to reduce body fat through exercise and low fat diet. An invention compound can help a human reduce body fat and through treatment of domestic edible animals such as cattle, swine, sheep, goats, turkeys and chickens can provide leaner meats for human consumption.

SUMMARY OF THE INVENTION

This invention provides new compounds of formula (II):

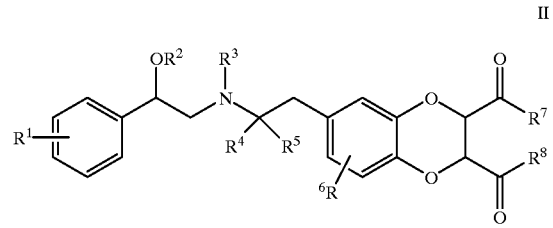

wherein $R^1$ and $R^6$ are independently hydrogen, $C_1$ to $C_6$ alkyl, trifluoromethyl, cyano, $C_1$ to $C_6$ alkoxy, or halogen;

$R^2$ is hydrogen or $C_1$ to $C_6$ trialkylsilyl; $R^3$ is hydrogen or $C_1$ to $C_6$ alkoxycarbonyl; or $R^2$ and $R^3$ are joined to form the oxazolidinone ring

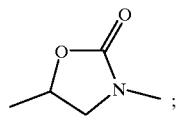

$R^4$ and $R^5$ are independently hydrogen or $C_1$ to $C_6$ alkyl;
$R^7$ and $R^8$ are independently OR$^9$ or NR$^{10}$R$^{11}$;
$R^9$ is hydrogen, $C_1$ to $C_{12}$ alkyl, $C_1$ to $C_{12}$ cycloalkyl, $C_1$ to $C_{12}$ silylalkyl, phenyl, naphthyl, phenyl $C_1$ to $C_6$ alkyl, $C_1$ to $C_6$ alkoxy $C_1$ to $C_6$ alkyl, pyridyl, thiophenyl, furanyl, imidazolyl, oxazolyl, —CHR$^{12}$COOR$^{13}$, —CHR$^{12}$C(O)R$^{13}$, —CHR$^{12}$CONR$^{10}$R$^{11}$, —CHR$^{12}$OCOOR$^{13}$, or —CHR$^{12}$OC(O)R$^{13}$;

$R^{10}$ and $R^{11}$ are independently hydrogen, $C_1$ to $C_{12}$ alkyl, phenyl, naphthyl, phenyl-$C_1$ to $C_6$ alkyl, furanylalkyl, or alkoxycarbonylalkyl;

$R^{12}$ and $R^{13}$ are independently hydrogen, $C_1$ to $C_{12}$ alkyl, phenyl, naphthyl, or phenyl-$C_1$ to $C_6$ alkyl; and the pharmaceutically acceptable salts thereof, the salts thereof;

the enandomers thereof, the racemic mixtures thereof, and the diastereomeric mixtures thereof.

Acid addition salts on an invention compound where a basic nitrogen is present can be prepared using a pharmaceutically acceptable inorganic or organic acid such as, but not limited to, hydrochloric, hydrobromic, sulfuric, phosphoric, acetic, fumaric, maleic, succinic, benzoic, methanesulfonic or toluenesulfonic acid. Base addition salts can be prepared where the invention compound has a carboxylic acid group from an alkali metal oxide or hyrdoxide or alkaline earth metal oxide or hydroxide such as NaOH, KOH, Ca(OH)$_2$.

The $\beta_3$ selective compounds of this invention are useful for the treatment of non-insulin dependent diabetes mellitus, hyperglycemia and obesity in mammals. β adrenergic receptors can be divided into $\beta_1$, $\beta_2$, and $\beta_3$ subtypes. Activation of $\beta_1$, receptors invokes increase in heart rate while activation of $\beta_2$ receptors stimulates glycogen breakdown in muscle and therefore prevents glycogen synthesis. Activation of $\beta_3$ receptors stimulates lipolysis or the breakdown of brown adipose tissue triglycerides to glycerol and free fatty acids, and therby promotes the loss of fat mass. Compounds that stimulate $\beta_3$ receptors will have anti-obesity activity. Brown adipose tissue may also play a role in glucose homeostasis and $\beta_3$ adrenergic agonist may therefore also have hypoglycemic or anti-diabetic activity.

In addition to the $\beta_3$ stimulating compounds, this invention provides for a method of treating obesity, hyperglycemia, and diabetes in mammals as well as a pharmaceutical composition. In addition to treating obesity in humans for health benefit, the invention compounds may offer further health benefit in humans by use in reducing fat in meat of animals raised for human consumption such as cattle, poultry, swine, sheep and goats.

DETAILED DESCRIPTION OF THE INVENTION

The compounds of the present invention may be prepared according to one of the general processes outlined below. As outlined in Scheme I, a catechol 1 is treated with a base and a dibromosuccinate ester 2 to afford an oxazolidinone 3, which is hydrolyzed to yield a 1,4-benzodioxine dicarboxylic acid 4, wherein $R^1$, $R^4$, $R^5$, and $R^6$, are as defined above. Syntheses of the starting catechol 1 is described in U.S. Pat. No. 5,061,727 and U.S. Pat. No. 5,420,291.

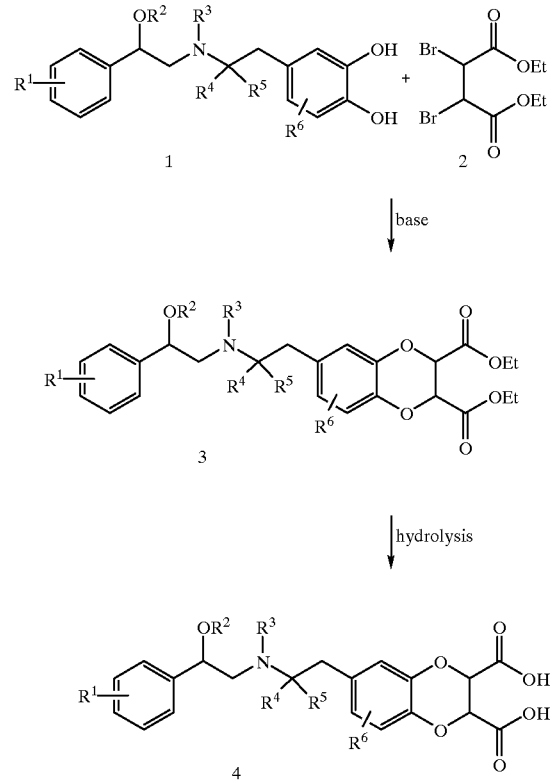

As outlined in Scheme II below, a disodium carboxylate 4 is converted to a disilver carboxylate and treated with an iodo derivative 5 to yield the diester compounds 6 wherein $R^1$, $R^4$, $R^5$, $R^6$, $R^{12}$, and $R^{13}$ are as defined above.

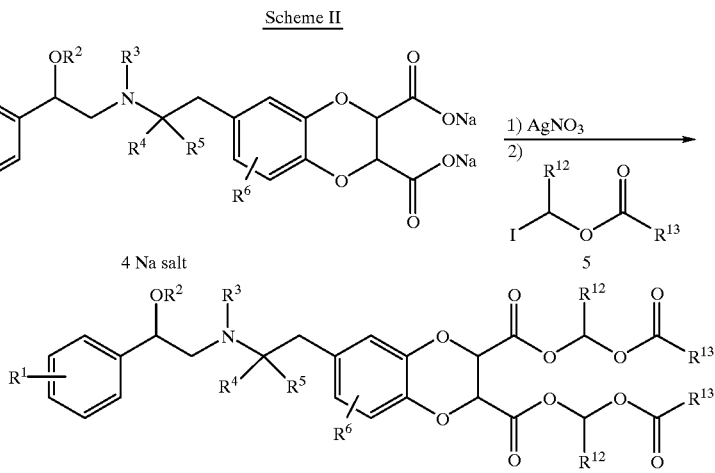

Scheme III below illustrates an alternative procedure for diester preparation wherein a dicarboxylic acid 4 is treated with an alcohol $R^9OH$ and an acid catalyst to yield the diester compounds 7 wherein $R^1$, $R^4$, $R^5$, $R^6$, and $R^9$ are as defined above.

As illustrated in Scheme V which follows, a diester compound 7 is reacted with an amine $HNR^{11}R^{12}$ to yield the diamide compounds 9, wherein $R^1$, $R^4$, $R^5$, $R^6$, $R^9$, $R^{11}$, and $R^{12}$ are as defined above.

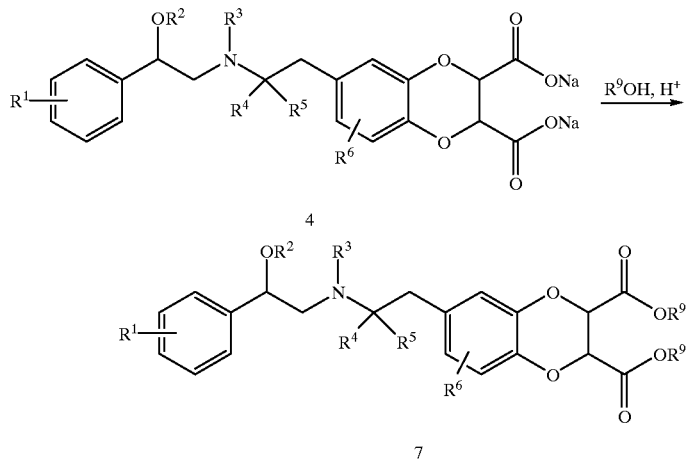

Scheme III

As outlined in Scheme IV below, the diester compounds 7 can be hydrolyzed under basic conditions to a monoester 8a and/or 8b, wherein $R^1$, $R^4$, $R^5$, $R^6$, and $R^9$ are as defined above. One or both of the regioisomers 8a and 8b may be produced in the hydrolysis reaction.

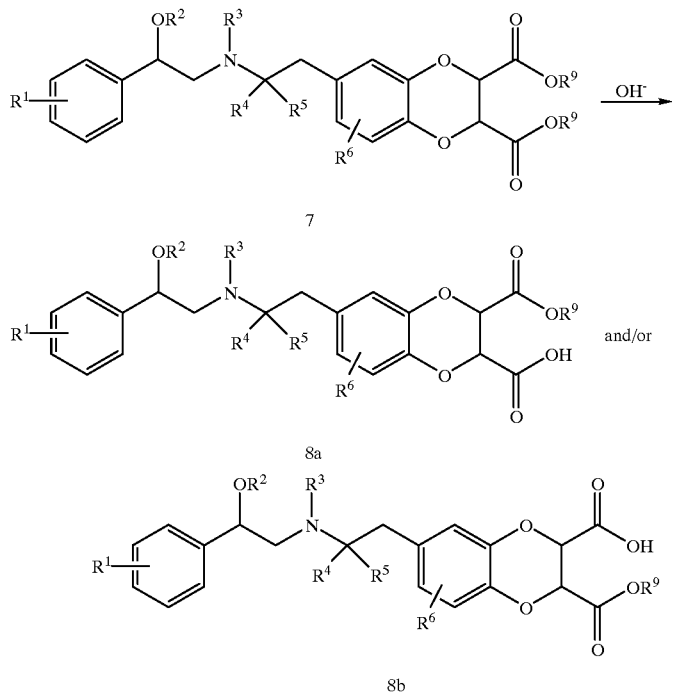

Scheme IV

Scheme IV

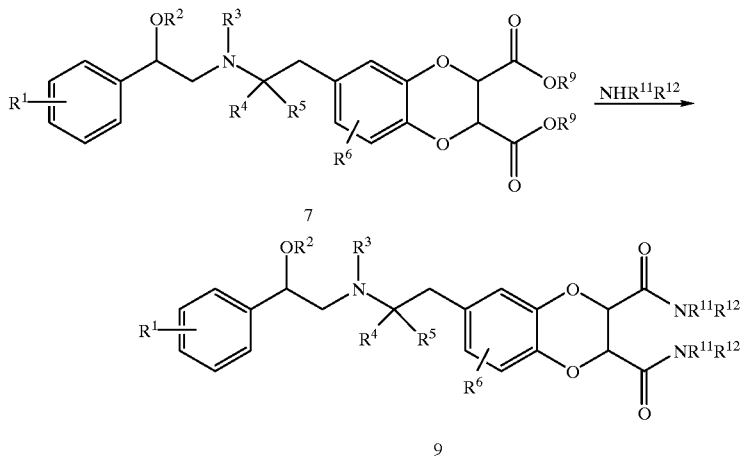

The following specific examples are included for illustration of the preparative procedures and are not to be construed as limiting to this disclosure in any way. The reagents and intermediates are either commercially available or readily prepared according to standard literature procedures by those skilled in the art of organic synthesis. Those skilled in the art may be aware of still other procedures for preparing compounds of this invention.

EXAMPLE 1

6-{(2R)-2-[(5R)-5-(3-Chloro-phenyl)-2-oxo-oxazolidin-3-yl]-propyl}-2, 3-dihydro-benzo[1,4]dioxine-2,3-dicarboxylic acid dimethyl ester A mixture of (R,R)-(±)-5-(3-chlorophenyl)-3-(2-(3,4-dihydroxyphenyl)-1-methylethyl)-2-oxazoldinone (3.47 g, 10 mmol), meso 1,2-dibromo dimethyl succinate (3,06 g, 10 mmol) and anhydrous $K_2CO_3$ was refluxed in acetone for six hours. The reaction mixture was then filtered and the residue was washed with acetone. The combined acetone filtrate was concentrated and the crude product obtained was purified by silica-gel column chromatography by eluting it with 3:1 hexine: ethylacetate. Pale yellow liquid. Yield 2.8 g (57%) $M^+H$.

EXAMPLE 2

6-{2-5-(3-Chloro-phenly-2-oxo-oxazolidin-3-yl]-propyl}-2,3-dihydro-benzo[1,4]dioxine-2,3-dicarboxylic acid 3-methyl ester To a stirred ethanolic solution of 6-{(2R)-2-[(5R)-5-(3-chloro-phenyl)-2-oxo-oxazolidin-3-yl]-propyl}-2,3-dihydro-benzo[1,4] dioxine-2,3-dicarboxylic acid dimethyl ester, (2.4 g, 5 mmol) sodium hydroxide (1.0 g, 25 mmol) was added. The reaction mixture was stirred for 8 hrs at room temperature. The reaction mixture was then concentrated and dissolved in water (100 ml). Concentrated hydrochloric acid was added and the separated compound was extracted with chloroformn; washed well with water, dried over anhydrous magnesium sulfate; filtered and concentrated. The product was purified by silica-gel column chromatography by eluting it with chloroform. Yield: 2.0 g solid; mp 198° C.; $M^+H$ 476.

EXAMPLE 3

(2,3-cis)-6-{(2R)-2-[(2R)-2-(3-Chloro-phenyl)-2-hydroxy-ethylamino]-propyl}-2,3-dihydro-benzo[1, 4]dioxine-2,3-dicarboxylic acid 6-{(2R)-2-[(5R)-5-(3-Chloro-phenyl)-2-oxo-oxazolidin-3-yl]-propyl}-2, 3-dihydro-benzo[1,4] dioxine-2,3-dicarboxylic acid dimethyl ester, (2.4 g, 5 mmol) and sodium hydroxide (1.0 g, 25 mmol) were refluxed in ethanol: water (9:1, 50 ml) for seventy-two hours. The reaction mixture was concentrated and the residue was dissolved in water (50 ml). It was neutralized with 1N HCl and the separated solid was filtered; washed well with water and air dried. It was found to be pure enough for further transformations.

Yield: 2.0 g; mp 220° C.; $M^+H$ 436.

EXAMPLE 4

(2,3-cis)-6-{(2R)-2-[(2R)-2-(3-Chloro-phenyl)-2-hydroxy-ethylamino]-propyl-2,3-dihydro-benzo[1,4]dioxine-2,3-dicarboxylic acid diisopropyl ester

EXAMPLE 5

(2,3-cis)-6-{(2R)-2-[(2R)-2-(3-Chloro-phenyl)-2-hydroxy-ethylamino]-propyl}-2,3-dihydro-benzo[1, 4]dioxine-2,3-dicarboxylic acid 3-isopropyl ester Hydrogen chloride gas was passed through isopropanol (100 ml) at 0° C. for fifteen minutes and the (2,3-cis)-6-{(2R)-2-[(2R)-2-(3-chloro-phenyl)-2-hydroxy-ethylamino]-propyl}2,3-dihydro-benzo[1,4]dioxine-2,3-dicarboxylic acid (2.15 g, 5 mmol) was added. The reaction mixture was refluxed for twenty-four hours and it was concentrated. The residue obtained was neutralized with sodium bicarbonate solution and extracted with chloroform. It was dried over anhydrous sodium sulfate; filtered and concentrated. The product obtained was purified by silica-gel column chromatography by eluting it initially with chloroform and then with chloroform:methanol (9:1). The diester eluted out first and it was followed by the monoester.

(2,3-cis)-6-{(2R)-2-[(2R)-2-(3-Chloro-phenyl)-2-hydroxy-ethylamino]-propyl-2,3dihydro-benzo[1,4]dioxine-2,3-dicarboxylic acid diisopropyl ester.

Amorphous; Yield 850 mg( 32%); $M^+H$ 520.

(2,3-cis)-6-{(2R)-2-[(2R)-2-(3-Chloro-phenyl)-2-hydroxy-ethylamino]-propyl}-2,3-dihydro-benzo[1,4]dioxine-2,3-dicarboxylic acid-3-isopropyl ester.

Amorphous; Yield 700 mg (29%) $M^+H$ 478.

General Procedure to Prepare (2,3-cis)-6-{(2R)-2-[(2R)-2-(3-Chloro-phenyl)-2-hydroxy-ethylamino]-propyl}-2, 3-dihydro-benzo[1,4]dioxine-2,3-dicarboxylic acid alkyl and cycloalkyl esters.

Hydrogen chloride gas was passed through the appropriate alcohol (100 ml) at 0° C. for fifteen minutes and the (2,3-cis)-6-{(2R)-2-[(2R)-2-(3-chloro-phenyl)-2-hydroxy-ethylarino]-propyl}2,3-dihydro-benzo[1,4] dioxine-2,3-dicarboxylic acid (2.15 g, 5 mmol) was added. The reaction mixture was heated to 100° C. for forty-eight hours. At the end, excess alcohol was removed under reduced pressure and the residue was neutralized with sodium bicarbonate solution. The product obtained was extracted with chloroform; washed well with water, dried over anhydrous magnesium sulfate; filtered and concentrated. The products were purified by silica-gel column chromatography. Initially the column was eluted with chloroform and later with 9:1 chloroform:methanol.

EXAMPLE 6

(2,3-cis-)-6-{(2R)-2-[(2R)-2-(3-Chloro-phenyl)-2-hydroxy-ethylamino]-propyl}-2,3-dihydro-benzo[1,4]dioxine-2,3-dicarboxylic acid dibutyl ester The tide compound was prepared from (2,3-cis)-6-{(2R)-2-[(2R)-2-(3-chloro-phenyl)-2-hydroxy-ethylamino]-propyl}2,3-dihydro-benzo[1,4] dioxine-2,3-dicarboxylic acid (2.15 g, 5 mmol) and n-butanol according to the General Procedure above to yield a brown oil: 1.1 g (40%); $M^+H$ 548.

EXAMPLE 7

(2,3-cis)-6-{(2R)-2-[(2R)-2-(3-Chloro-phenyl)-2-hydroxy-ethylamino]-propyl}-2,3-dihydro-benzo[1,4]dioxine-2,3-dicarboxylic acid bis-(2-ethoxy-ethyl) ester The title compound was prepared from (2,3-cis)-6-{(2R)-2-[(2R)-2-(3-chloro-phenyl)-2-hydroxy-ethylamino]-propyl}2,3-dihydro-benzo[1,4] dioxine-2,3-dicarboxylic acid (2.15 g, 5 mmol) and 2-ethoxyethanol. Two diastereomers were obtained as amorphous solids: diastereomer 1: Yield 800 mg (33%) $M^+H$ 480. diasteromer 2: Yield 600 mg (25%) $M^+H$ 480.

EXAMPLE 8

(2,3-cis)-6-{(2R)-2-[(2R)-2-(3-Chloro-phenyl)-2-hydroxy-ethylamino]-propyl}-2,3-dihydro-benzo[1,4]dioxine-2,3-dicarboxylic acid diethyl ester The title compound was prepared from (2,3-cis)-6-{(2R)-2-[(2R)-2-(3-chloro-phenyl)-2-hydroxy-ethylamino]-propyl}2,3-dihydro-benzo[1,4] dioxine 2,3-dicarboxylic acid (2.15 g, 5 mmol) and ethanol according to the General Procedure above to yield a brown oil: 600 mg (24%); $M^+H$ 492.

EXAMPLE 9

(2,3-cis)-6-{(2R)-2-[(2R)-2-(3-Chloro-phenyl)-2-hydroxy-ethylamino]-propyl}-2,3-dihydro-benzo[1,4]dioxine-2,3-dicarboxylic acid dicyclohexyl ester The title compound was prepared from (2,3-cis)-6-{(2R)-2-[(2R)-2-(3-chloro-phenyl)-2-hydroxy-ethylamino]-propyl}2,3-dihydro-benzo[1,4] dioxine-2,3-dicarboxylic acid (2.15 g, 5 mmol) and cyclohexanol according to the General Procedure above to yield a brown foam: 750 mg (40%); $M^+H$ 600.

EXAMPLE 10

(2,3-cis)-6-{(2R)-2-[(2R)-2-(3-Chloro-phenyl)-2-hydroxy-ethylamino]-propyl}-2,3-dihydro-benzo[1,4]dioxine-2,3-dicarboxylic acid dicyclopentyl ester The title compound was prepared from from (2,3-cis)-6-{(2R)-2-[(2R)-2-(3-chloro-phenyl)-2-hydroxy-ethylamino]-propyl}2,3-dihydro-benzo[1,4] dioxine-2,3-dicarboxylic acid (2.15 g, 5 mmol) and cyclopentanol according to the General Procedure above to yield an amorphous solid: 1.4g (49%); $M^+H$ 572.

EXAMPLE 11

(2,3-cis)-6-{(2R)-2-[(2R)-2-(3-Chloro-phenyl)-2-hydroxy-ethylamino]-propyl}-2,3-dihydro-benzo]1,4]-dioxine-2,3-dicarboxylic acid dioctyl ester The title compound was prepared from from (2,3-cis)-6-{(2R)-2-[(2R)-2-(3-chloro-phenyl)-2-hydroxy-ethylamino]-propyl}2,3-dihydro-benzo[1,4] dioxine-2,3-dicarboxylic acid (2.15 g, 5 mmol) and 1-octanol according to the General Procedure above to yield a brown foam: 1.3 g (39%); $M^+H$ 660.

EXAMPLE 12

(2,3-cis)-6-{(2R)-2-[(2R)-2-(3-Chloro-phenyl)-2-hydroxy-ethylamino]-propyl}-2,3-dihydro-benzo[1,4]-dioxine-2,3-dicarboxylic acid dibenzyl ester The title compound was prepared from from (2,3-cis)-6-{(2 R)-2-[(2R)-2-(3-chloro-phenyl)-2-hydroxy-ethylamino]-propyl}2,3-dihydro-henzo[ 1,4] dioxine-2,3-dicarboxylic acid (2.15 g, 5 mmol) and benzyl alcohol according to the General Procedure above to yield a brown oil: 1.0 g(32%); $M^+H$ 616.

Human Beta Adrenergic Receptor Selectivity

The activity of the test compounds on human β-adrenergic receptors was determined with Chinese hamster ovary (CHO) cells transfected with human $\beta_3$, $\beta_2$, or $\beta_1$ adrenergic receptors. The preparation of these cells has been described in Emorine, L. J., Marullo, S., Briend-Sutren, M., Patey, G., Tate, K., Delavier-Klutchko, C., Strosberg, A. D. Molecular Characterization of the Human Beta 3-Adrenergic Receptor *Science* 1989,245(8), 1118–1121 and in Muzzin, P., Revelli, J.-P., Kuhne, F., Gocayne, J. D., McCombie, W. R., Venter, J. C., Giacobino, J.-P., Fraser, C. M. An Adipose Tissue-Specific Beta 3-Adrenergic Receptor. Molecular Cloning and Down-Regulation in Obesity *J. Biol. Chem.* 1991, 226, 24053–24058. Agonist activity is indicated by increased cAMP levels in the CHO cells. Selectivity of the test compounds for the $\beta_3$ receptor was assessed by comparison with results in $\beta_2$ and $\beta_1$ adrenergic receptor transfected cells.

Procedure

1). Chinese hamster ovary (CHO) cells transfected with human $\beta_3$, $\beta_2$, or $\beta_1$ adrenergic receptors were used in the assay.

2). Cells were grown to confluent conditions in 24 well plates.

3). Drugs were dissolved in DMSO at a concentration of 10 μM.

4). Cells were incubated with drug at 10 nM concentration for 10 min at 37° C. Isoproterenol (Standard 1) was used as the standard compound and assayed at 10 μM which gives a maximal cAMP elevation in all 3 cell types.

5). Cell cAMP concentrations were assayed using a scintillation proximity assay from Amersham Corp (Chicago, Ill.).

6). Activities for the test compounds are expressed as a percentage of the isoproterenol response.

Effects on Free Fatty Acid Levels in Rats

Rats respond to a single oral dose of $\beta_3$ agonist by increasing plasma free fatty acids (FFA) in response to $\beta_3$ receptor stimulation on the plasma membrane of the fat cell. 5-{2-[2-(3-Chloro-phenyl)-2-hydroxy-ethylamino]-propyl}-benzo[1,3]dioxole-2,2-dicarboxylic acid diisopropyl ester (Standard 2) was used as a standard compound. All test compounds were dosed at 0.1 mg/kg and compared to the response by Standard 2.

Procedure

1). Drugs were dissolved in DMSO at 10 mg/mL.

2). Twenty µl of the DMSO-drug solution was added to 10 mL methyl cellulose:Tween-80 (0.5%:0.1%) for a final concentration of 20 µg/mL.

3). Methyl cellulose:tween-80 drug suspension was given via gavage (1 mL/200 g body weight; or 0.1 mg/kg) to rats and blood was collected 50 min later.

4). Plasma was analyzed for free fatty acids using a kit supplied by Biochemical Diagnostics Inc. (Brentwood, N.Y.).

5). Drug response was calculated from the formula below.

$$\% \text{FFA Response} = \frac{\text{FFA (compound)} - \text{FFA vehicle}}{\text{FFA (Standard 2)} - \text{FFA vehicle}} \times 100$$

Effects on Hyperglycemia in Mice

On the morning of Day 1 (baseline), 35 mice (male, db/db (C57BL/KsJ), Jackson Laboratories, 2 to 7 months of age and 35 to 60 g) were fasted for 4 h, weighed, and a baseline blood sample was collected from the tail-tip of each mouse without anesthesia, placed directly into a fluoride-containing tube, mixed, and maintained on ice. Food was then returned to the mice. The plasma was seperated and the levels of glucose in the plasma were dertermined by an Abbot VP Analyzer. Because of the variable plasma glucose levels of the db/db mice, the 5 mice having the most extreme (i.e., highest or lowest) plasma glucose levels were excluded and the remaining 30 mice were randomly assigned into 7 groups of equivalent mean plasma glucose level (vehicle control, ciglitazone (Standard 3), and 5 test compound groups). On the afternoon of Days 1, 2, and 3 the vehicle (0.2 mL of 2% Tween 80/saline w/v) or test compounds were administered (p.o.) to the ad libitum fed mice. On the morning of Day 4, the food was removed from the cages for 3 h, a blood sample was collected, and the mice were then given the fourth administration of test compound or vehicle. Additional blood samples were collected at 2 and 4 h after test compound administration. Plasma glucose levels were determined. To assess test compound activity, the percent change of an animal's plasma glucose level on Day 4 (mean of 2 and 4 h values) from its level before test compound administration (Day 1 baseline sample) was determined as follows:

$$\frac{\text{Mean of 2 and 4 h samples (Day 4)}}{\text{Baseline sample (Day 1)}} \times 100$$

A 50–60% reduction of plasma glucose levels in the hyperglycemic db/db mice represents a normalization of glucose levels.

TABLE I

| Compound (Example) | $\beta_2{}^a$ | $\beta_3{}^a$ | Rat Free Fatty Acid[b] |
|---|---|---|---|
| 4 | 9% | 4% | 32% |
| 5 | 11% | 50% | 6% |
| 6 | 16% | 51% | 0% |
| 7 | 33% | 40% | 7% |
| 8 | — | — | 19% |
| 9 | 1% | 3% | 3% |
| 10 | 4% | 3% | 20% |
| 11 | 38% | 97% | 5% |
| 12 | 11% | 27% | 11% |

[a]Human $\beta$ receptors expressed in Chinese hamster ovary cells, compounds tested at 10 nM, results expressed as % of isoproterenol activity (increase in cAMP) at 10 µM.
[b]Elevation of plasma free fatty acids in rats, compounds tested at 0.1 mg/kg, results expressed as % of 5-{2-[2-(3-chloro-phenyl)-2-hydroxy-ethylamino]-propyl}-benzo[1,3]dioxole-2,2-dicarboxylic acid diisopropyl ester response (78% increase) at 0.1 mg/kg.

Pharmaceutical Composition

Compounds of this invention may be administered neat or with a pharmaceutical carrier to a patient in need thereof. The pharmaceutical carrier may be solid or liquid.

Applicable solid carriers can include one or more substances which may also act as flavoring agents, lubricants, solubilizers, suspending agents, fillers, glidants, compression aids, binders or tablet-disintegrating agents or an encapsulating material. In powders, the carrier is a finely divided solid which is in admixture with the finely divided active ingredient. In tablets, the active ingredient is mixed with a carrier having the necessary compression properties n suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers may be used in preparing solutions, suspensions, emulsions, syrups and elixirs. The active ingredient of this invention can be dissolved or suspended in a pharmaceutically acceptable liquid carrier such as water, an organic solvent, a mixture of both or pharmaceutically acceptable oils or fat. The liquid carrier can contain other suitable pharmaceutical additives such a solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (particularly containing additives as above, e.g., cellulose derivatives, preferable sodium carboxymethyl cellulose solution), alcohols (including monohydric alcohols and polyhydric alcohols, e.g., glycols) and their derivatives, and oils (e.g., fractionated coconut oil and arachis oil). For parenteral administration the carrier can also be an oily ester such as ethyl oleate and isopropyl myristate. Sterile liquid carriers are used in sterile liquid form compositions for parenteral administration.

Liquid pharmaceutical compositions which are sterile solutions or suspensions can be utilized by, for example, intramuscular, intraperitoneal or subcutaneous injection. Sterile solutions can also be administered intravenously. Oral administration may be either liquid or solid composition form.

The compounds of this invention may be administered rectally in the form of a conventional suppository. For administration by intranasal or intrabronchial inhalation or insufflation, the compounds of this invention may be formulated into an aqueous or partrially aqueous solution, which can then be utilized in the form of an aerosol. The compounds of this invention may also be administered transdermally through the use of a transdermal patch containing the active compound and a carrier that is inert to the active compound, is non-toxic to the skin, and allows delivery of the agent for systemic absorption into the blood stream via the skin. The carrier may take any number of forms such as creams and ointments, pastes, gels, and occlusive devices. The creams and ointments may be viscous liquid or semi-solid emulsions of either the oil in water or water in oil type. Pastes comprised of absorptive powders dispersed in petroleum or hydrophilic petroleum containing the active ingredient may also be suitable. A variety of occlusive devices may be used to release the active ingredient into the blood stream such as a semipermeable membrane covering a reservoir containing the active ingredient with or without a carrier, or a matrix containing the active ingredient. Other occlusive devices are known in the literature. Further, an invention compound may be incorporated into a controlled release subcutaneous implant for gradual release over a period of time eliminating the necessity of frequent dosing. An antiobesity invention compound may also be incorporated into animal feed for the use with livestock as a means of oral dosing.

In addition the compounds of this invention may be employed as a solution, cream, or lotion by formulation with pharmaceutically acceptable vehicles containing 0.1–5%, preferably 2% of active compound which may be administered to a fungally effected area.

The dosage to be used in the treatment of a specific patient suffering obesity and/or diabetes and/or hyperglycemia must be subjectively determined by the attending physician. The variables involved include the severity of the dysfunction, and the size, age, and response pattern of the patient. Treatment will generally be initiated with small dosages less than the optimum dose of the compound. Thereafter the dosage is increased until the optimum effect under the circumstances is reached. Precise dosages for oral, parenteral, nasal, or intrabronchial administration will be determined by the administering physician based on experience with the individual subject treated and standerd madical principles.

Preferably the pharmaceutical composition is in unit dosage form, e.g., as tablets or capsules. In such form, the composition is sub-divided in unit dose containing appropriate quantities of the active ingredient; the unit dosage form can be packaged compositions, for example packed powders, vials, ampoules, prefilled syringes or sachets containing liquids. The unit dosage form can be, for example, a capsule or tablet itself, or it can be the appropriate number of any such compositions in package form.

What is claimed:
1. A method of treating diabetes and/or hyperglycemia in a mammal having diabetes or hyperglycemia which comprises administering to said mammal a therapeutically effective amount of a compound having the formula:

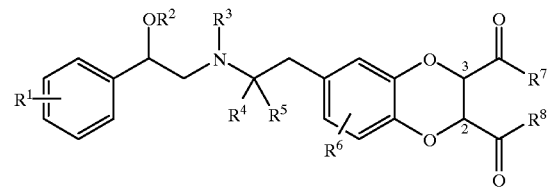

wherein $R^1$ and $R^6$ are independently hydrogen, $C_1$ to $C_6$ alkyl, trifluoromethyl, cyano, $C_1$ to $C_6$ alkoxy, or halogen;

$R^2$ is hydrogen;

$R^3$ is hydrogen or $C_1$ to $C_6$ alkoxycarbonyl;

$R^4$ and $R^5$ are independently hydrogen or $C_1$ to $C_6$ alkyl;

$R^7$ and $R^8$ are independently $OR^9$ or $NR^{10}R^{11}$;

$R^9$ is hydrogen, $C_1$ to $C_{12}$ alkyl, $C_3$ to $C_{12}$ cycloalkyl, phenyl, naphthyl, phenyl, $C_1$ to $C_6$ alkyl, $C_1$ to $C_6$ alkoxy, $C_1$ to $C_6$ alkyl, thiophenyl, furanyl, $-CHR^{12}COOR^{13}$, $-CHR^{12}C(O)R^{13}$, $-CHR^{12}CONR^{10}R^{11}$, $-CHR^{12}OCOOR^{13}$, or $-CHR^{12}OC(O)R^{13}$;

$R^{10}$ and $R^{11}$ are independently hydrogen, $C_1$ to $C_{12}$ alkyl, phenyl, naphthyl, phenyl-$C_1$ to $C_6$ alkyl, furanylalkyl, or alkoxycarbonylalkyl;

$R^{12}$ and $R^{13}$ are independently hydrogen, $C_1$ to $C_{12}$ alkyl, phenyl, naphthyl, or phenyl-$C_1$ to $C_6$ alkyl; and the pharmaceutically acceptable salts thereof, an enantiomer or diastereomer thereof, or a pharmaceutically acceptable salt thereof.

2. The method of claim 1 wherein said compound is (2,3-cis)-6-{(2R)-2-[(2R)-2-(3-chloro-phenyl)-2-hydroxy-ethylamino]-propyl}-2,3-dihydro-benzo[1,4]dioxine-2,3-dicarboxylic acid or a pharmaceutically acceptable salt thereof.

3. The method of claim 1 wherein said compound is (2,3-cis)-6-{(2R)-2-[(2R)-2-(3-chloro-phenyl)-2-hydroxy-ethylamino]-propyl}-2,3-dihydro-benzo[1,4]dioxine-2,3-dicarboxylic acid diisopropyl ester or a pharmaceutically acceptable salt thereof.

4. The method of claim 1 wherein said compound is (2,3-cis)-6-{(2R)-2-[(2R)-2-(3-chloro-phenyl)-2-hydroxy-ethylamino]-propyl}-2,3-dihydro-benzo[1,4]dioxine-2,3-dicarboxylic acid 3-isopropyl ester or a pharmaceutically acceptable salt thereof.

5. The method of claim 1 wherein said compound is (2,3-cis)-6-{(2R)-2-[(2R)-2-(3-chloro-phenyl)-2-hydroxy-ethylamino]-propyl}-2,3-dihydro-benzo[1,4]dioxine-2,3-dicarboxylic acid dibutyl ester or a pharmaceutically acceptable salt thereof.

6. The method of claim 1 wherein said compound is (2,3-cis)-6-{(2R)-2-[(2R)-2-(3-chloro-phenyl)-2-hydroxy-ethylamino]-propyl}-2,3-dihydro-benzo[1,4]dioxine-2,3-dicarboxylic acid bis-(2-ethoxy-ethyl) ester or a pharmaceutically acceptable salt thereof.

7. The method of claim 1 wherein said compound is (2,3-cis)-6-{(2R)-2-[(2R)-2-(3-chloro-phenyl)-2-hydroxy-ethylamino]-propyl}-2,3-dihydro-benzo[1,4]dioxine-2,3-dicarboxylic acid diethyl ester or a pharmaceutically acceptable salt thereof.

8. The method of claim 1 wherein said compound is (2,3-cis)-6-{(2R)-2-[(2R)-2-(3-chloro-phenyl)-2-hydroxy-ethylamino]-propyl}-2,3-dihydro-benzo[1,4]dioxine-2,3-dicarboxylic acid dicyclohexyl ester or a pharmaceutically acceptable salt thereof.

9. The method of claim 1 wherein said compound is (2,3-cis)-6-{(2R)-2-[(2R)-2-(3-chloro-phenyl)-2-hydroxy-ethylamino]-propyl}-2,3-dihydro-benzo[1,4]dioxine-2,3-dicarboxylic acid dicyclopentyl ester or a pharmaceutically acceptable salt thereof.

10. The method of claim 1 wherein said compound is (2,3-cis)-6-{(2R)-2-[(2R)-2-(3-chloro-phenyl)-2-hydroxy-ethylamino]-propyl}-2,3-dihydro-benzo[1,4]dioxine-2,3-dicarboxylic acid dioctyl ester or a pharmaceutically acceptable salt thereof.

11. The method of claim 1 wherein said compound is (2,3-cis)-6-{(2R)-2-[(2R)-2-(3-chloro-phenyl)-2-hydroxy-ethylamino]-propyl}-2,3-dihydro-benzo[1,4]dioxine-2,3-dicarboxylic acid dibenzyl ester or a pharmaceutically acceptable salt thereof.

* * * * *